(12) United States Patent
Buhr et al.

(10) Patent No.: US 8,052,969 B2
(45) Date of Patent: Nov. 8, 2011

(54) METHOD OF MAKING PLASMA ENRICHED WITH PLATELETS USING A DOUBLE SYRINGE SYSTEM WHERE THE SECOND SYTRINGE IS WITHIN THE FIRST SYRINGE AND USE THEREOF

(75) Inventors: Michael Buhr, Bonn (DE); Werner Siekmann, Hamburg (DE); Stèphane Naudin, Planegg (FR)

(73) Assignee: Arthrex, Inc., Naples, FL (US)

( * ) Notice: Subject to any disclaimer, the term of this patent is extended or adjusted under 35 U.S.C. 154(b) by 990 days.

(21) Appl. No.: 11/963,554

(22) Filed: Dec. 21, 2007

(65) Prior Publication Data

US 2008/0166421 A1    Jul. 10, 2008

Related U.S. Application Data

(60) Provisional application No. 60/877,406, filed on Dec. 28, 2006.

(51) Int. Cl.
*A01N 63/00* (2006.01)

(52) U.S. Cl. .................................................... 424/93.72

(58) Field of Classification Search ........................ None
See application file for complete search history.

(56) References Cited

U.S. PATENT DOCUMENTS

| | | | |
|---|---|---|---|
| 4,936,315 A | 6/1990 | Lineback | |
| 5,165,938 A | 11/1992 | Knighton | |
| 5,178,883 A | 1/1993 | Knighton | |
| 5,395,325 A | 3/1995 | Moreno et al. | |
| 5,489,267 A | 2/1996 | Moreno et al. | |
| 5,902,608 A | 5/1999 | Read et al. | |
| 6,716,187 B1 | 4/2004 | Jorgensen et al. | |
| 6,811,777 B2 | 11/2004 | Mishra | |
| 7,314,617 B2 | 1/2008 | Mishra | |
| 7,452,344 B2 | 11/2008 | Jorgensen et al. | |
| 2005/0186193 A1 | 8/2005 | Mishra | |
| 2008/0248083 A1 | 10/2008 | Mishra | |
| 2008/0248085 A1 | 10/2008 | Mishra | |

OTHER PUBLICATIONS

Merriam-Webster Medical Dictionary definition of plasma, accessed Apr. 8, 2011.*
Merrian-Webster Medical Dictionary definition of conditioned, accessed Apr. 8, 2011.*
Stedman's Medical Dictionary definition of syringe, accessed Apr. 8, 2011.*
Giles, "The Platelet Count and Mean Platelet Volume", British Journal of Haematology 48 (1) : 31-37 (1981).*
Aspenberg et al. "Platelet concentrate injection improves Achilles tendon repair in rats", Acta Orthop. Scand. 75(1) : 93-99 (2004).*

* cited by examiner

*Primary Examiner* — Sandra Saucier
(74) *Attorney, Agent, or Firm* — Dickstein Shapiro LLP

(57) ABSTRACT

A method of providing autologous conditioned plasma (ACP) for treatment of connective tissue injuries. The method comprises the steps of: (i) providing an apparatus comprising a centrifuge and a double syringe, the double syringe including an inner syringe body and an outer syringe body; (ii) drawing autologous blood into the outer syringe body; (iii) subjecting the autologous blood to at least one centrifugation step to obtain an autologous conditioned plasma (ACP); (iv) removing, with the inner syringe body, at least a portion of autologous conditioned plasma (ACP) from the outer syringe body; and (v) inject ACP for treatment of various cartilage or tendon damage or diseases.

13 Claims, 2 Drawing Sheets

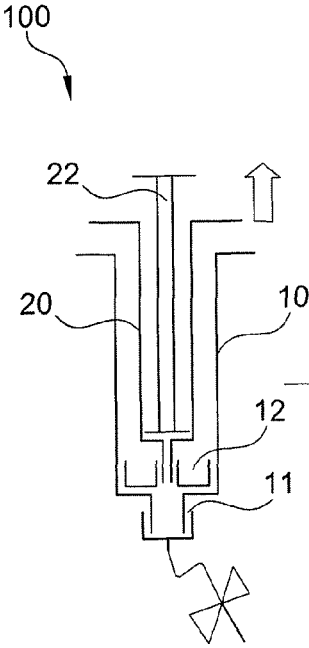
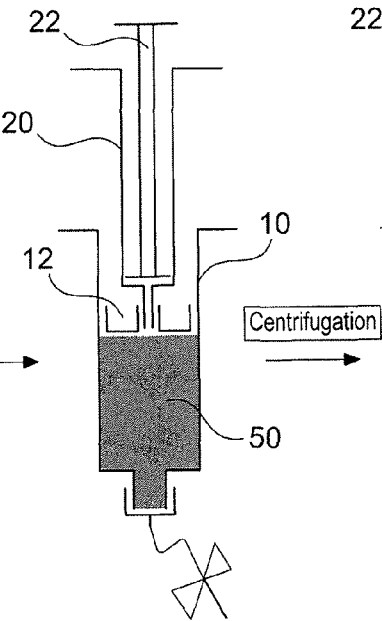
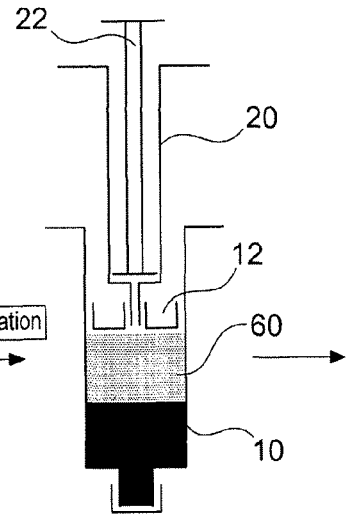
FIG. 1(a)   FIG. 1(b)   FIG. 1(c)
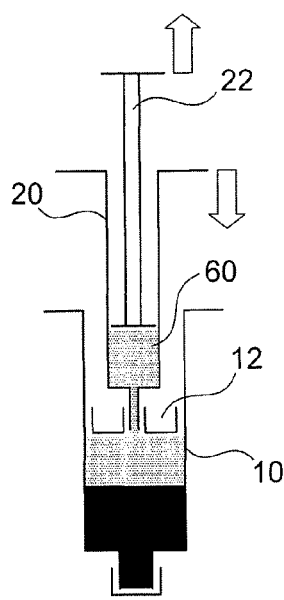
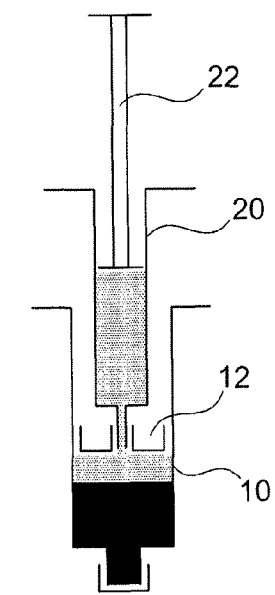
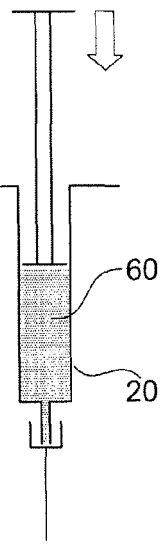
FIG. 1(d)   FIG. 1(e)   FIG. 1(f)

METHOD OF MAKING PLASMA ENRICHED WITH PLATELETS USING A DOUBLE SYRINGE SYSTEM WHERE THE SECOND SYTRINGE IS WITHIN THE FIRST SYRINGE AND USE THEREOF

CROSS REFERENCE TO RELATED APPLICATIONS

This application claims the benefit of U.S. Provisional Application Ser. No. 60/877,406 filed on Dec. 28, 2006, the entire disclosure of which is incorporated by reference in its entirety herein.

FIELD OF THE INVENTION

The present invention relates to methods and apparatus for the treatment of human or non-human damaged tissue using autologous conditioned plasma.

BACKGROUND OF THE INVENTION

Every healing process after an injury or an operation challenges the body's powers of regeneration. Platelets play a pivotal role in this regeneration. Not only do the platelets initiate the coagulation of the blood and thereby also wound closure, they also play an important part in tissue regeneration since they produce messenger substances, so-called growth factors. These growth factors attract stem cells and reserve cells and induce these to differentiate. Through this proliferation, the new tissue is then formed.

Growth factors act like a "magnet" on stem cells and reserve cells. If the power of this "magnet" is increased, more stem cells and reserve cells are attracted and healing time is reduced.

SUMMARY OF THE INVENTION

The present invention provides an apparatus for providing an autologous conditioned plasma (ACP) for treatment of human or non-human damaged tissue such as cartilage and neurological tissue. The apparatus comprises at least one syringe used in conjunction with a centrifuge for providing the autologous plasma that is injected into the damaged tissue. In an exemplary embodiment, the apparatus comprises two syringes that are used independently for storing and delivering the autologous plasma.

The present invention also provides a method of providing autologous growth factors for treatment of connective tissue injuries. The method comprises the steps of: (i) providing an apparatus comprising a centrifuge and a double syringe, the double syringe including an inner syringe body and an outer syringe body; (ii) drawing autologous blood into the outer syringe body; (iii) subjecting the autologous blood to at least one centrifugation step to obtain an autologous plasma; and (iv) removing, with the inner syringe body, at least a portion of autologous plasma from the outer syringe body.

Other features and advantages of the present invention will become apparent from the following description of the invention, which refers to the accompanying drawing.

BRIEF DESCRIPTION OF THE DRAWINGS

FIGS. 1(a)-(f) illustrate schematic views of a double syringe assembly of the present invention for obtaining autologous blood components in accordance with a first embodiment of the present invention;

DETAILED DESCRIPTION OF THE PREFERRED EMBODIMENTS

Figure 2A:
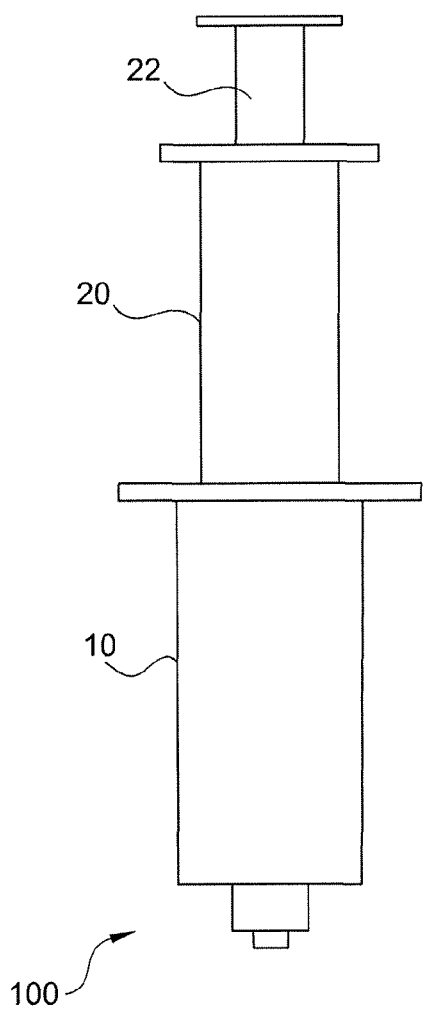
FIGS. 2(a) and 2(b) illustrate a side view and a cross-sectional view, respectively, of the double syringe assembly of FIG. 1(a)

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides an assembly for obtaining an autologous conditioned plasma (ACP) for treating damaged tissue without concern for the storage stability or patient compatibility. In an exemplary embodiment, the assembly comprises a double syringe (also referred to as a "two-chamber syringe"), for example an outer syringe body (a distal syringe) and an inner syringe body (a proximal syringe) located at least partially within the outer syringe body, or a first syringe (a proximal syringe) in direct fluid communication with a second syringe (a distal syringe).

According to an exemplary embodiment, blood is first obtained from a patient and stored in the outer syringe body. The blood is then separated to retrieve certain healing components such as platelets, to obtain an autologous conditioned plasma (ACP). At least part of the autologous conditioned plasma (ACP) is removed with the inner syringe. Preferably, the autologous conditioned plasma (ACP) has a platelet concentration factor of about 2 compared to the platelet concentration of the patient's normal blood. The removed plasma may be subsequently employed in surgical repairs, promoting the healing of the repair and promoting tissue growth in orthopedic and neurological applications, for example.

The term "growth factor" as used in the present application is intended to include all factors, such as proteinaceous factors, for example, which play a role in the induction or conduction of growth of tissue, ligaments, bone, cartilage or other tissues associated with bone or joints. In particular, the following sets forth the growth factors contained in platelets and their effects:

PDGF (Platelet-derived growth factor)—Stimulation of collagen synthesis, the formation of blood vessels and fibroblast proliferation; activation of macrophages and neutrophiles; activates TGF-$\beta$; attracts stem cells.

FGF (Fibroblast growth factor)—Stimulates the formation of blood vessels, collagen synthesis, wound contraction, matrix synthesis, epithelialisation.

TGF-$\beta$ (Transforming growth factor $\beta$)—Reduces scar formation; reduces wound healing disturbances caused by corticoids; attracts fibroblasts and promotes their proliferation; stimulates collagen synthesis; promotes the secretion of FGF and PDGF by monocytes.

TGF-$\alpha$ (Transforming growth factor-$\alpha$)—Stimulates mesenchymal, epithelial and endothelial cells.

EGF—(Epithelial Growth Factor)—Stimulates epithelialisation and the formation of new blood vessels.

Blood obtained from the patient is separated, using a centrifuge, for example, to retrieve certain healing components such as growth factors, to obtain an autologous conditioned plasma (ACP). Preferably, the autologous conditioned plasma (ACP) has a platelet concentration factor of about 2 compared to the platelet concentration of the patient's normal blood. For example, the autologous conditioned plasma (ACP) may contain about 470,000 platelet/microliter (for a donor) compared to the about 200,000 platelet/microliter of the donor's whole blood, and compared to the about 500,000-1,000,000 platelet/microliter of the platelet-rich plasma (PRP) (of the donor), and compared to about 0 platelet/microliter of the platelet-poor plasma (PPP) (of the donor).

This autologous conditioned plasma (ACP) may also comprise autologous growth factors as defined above. In a preferred embodiment, the term "growth factor" includes autologous growth factors produced from a patient's own blood, obtained by a centrifugation process.

Optionally, the autologous conditioned plasma may comprise additional antiseptic chemicals and/or antibiotics and/or electrolytes. The additional antiseptics and/or the antibiotics and/or the electrolytes will typically be present in the plasma in a predetermined concentration range, which will be dependent upon the particular tissue site and application, as well as the specific activity of the antiseptic and/or the antibiotic and/or the electrolytes. The antibiotics may be selected from the group consisting of a neosporin, vancomycin and gentamycin, and combinations thereof.

The autologous conditioned plasma may further comprise one or more additional components which promote or enhance the wound healing effectiveness of the autologous growth factors. As such, hormones or site-specific hybrid proteins may be incorporated in the autologous blood suspension to maximize the availability of the autologous growth factors at the tissue to be repaired and/or to potentiate wound healing.

According to another embodiment of the present invention, the autologous plasma may additionally comprise anticoagulants such as, for example, citrate, acid-citrate dextrose (ACD), citrate-phosphate-dextrose (CPD), or ethylene diamine tetra-acetic acid (EDTA). Heparin may be also added in an amount sufficient for the prevention of thrombin activity during the processing steps. Proteolytic enzyme inhibitors, such as aprotinin ε-aminocaproic acid or tranexamic acid may be added to prevent proteolytic degradation of the autogenous growth factors.

According to yet another embodiment of the present invention, the autologous plasma may further comprise one or more vitamins such as vitamin E, vitamin A and other retinoids. Vitamins are known to have wound healing and antioxidant properties. Alternatively, or additionally, non-vitamin anti-oxidants may be included in the blood suspension. Non-limiting representative examples of such anti-oxidants include β-carotene.

Figure 2B:
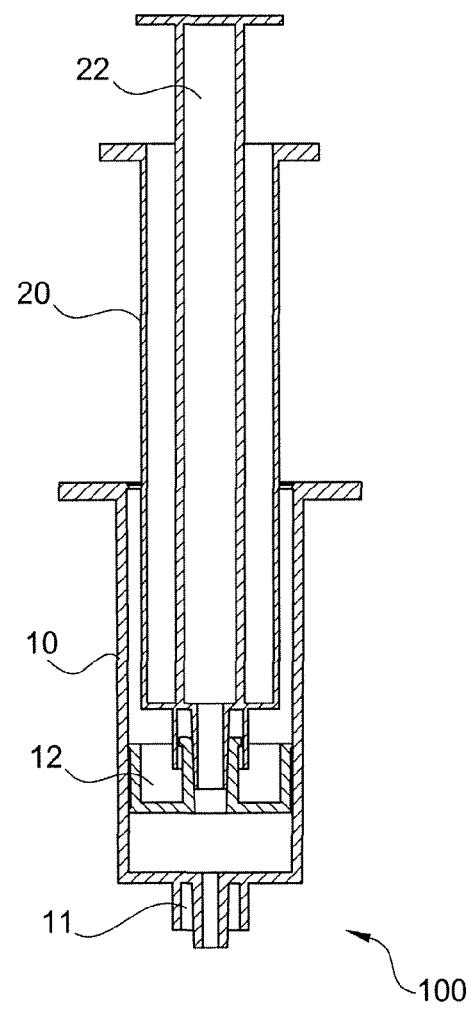
Figure 2C:
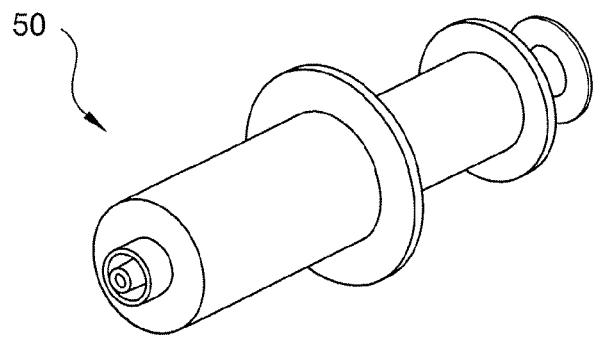
FIG. 2(c) illustrates a perspective view of the double syringe assembly of FIG. 2(a).

FIGS. 1(a)-(f), 2(a)-(c) and 3 illustrate apparatus 100, 200 for providing autologous conditioned plasma 60 for treatment of human or non-human damaged tissue such as cartilage and neurological tissue. Apparatus 100, 200 comprises a double-chamber syringe (also referred to as the "inner and outer syringe bodies") used in conjunction with a centrifuge for providing the autologous conditioned plasma (ACP) that is provided by injection, for example, into the damaged tissue. The double-chamber syringe may be also referred to as a "two-chamber syringe," for example an outer syringe body and an inner syringe body located at least partially within the outer syringe body. In another embodiment, apparatus 100, 200 may comprise a first syringe in direct fluid communication with a second syringe, one of the syringes being provided within at least a portion of the body of the other syringe.

In an exemplary embodiment and as illustrated in the figures, apparatus 100 comprises two chambers 10, 20 having different diameters to allow the body of one of the syringes to be at least partially located within the body of the other one of the syringes. As detailed below, outer syringe body 10 (distal syringe) is used to store the autologous conditioned plasma 60 formed as the result of the centrifugation of blood 50, while inner syringe body 20 (proximal syringe) is used to remove/extract at least part of autologous conditioned plasma 60 from the outer syringe body 10 and to further inject the removed part of autologous conditioned plasma 60 into the damaged tissue.

Outer syringe body 10 (distal syringe) may be in the form of a conventional syringe for obtaining a blood sample, including a body that is configured to accommodate a flow-through plunger 12. Outer syringe body 10 is also provided with a tip or coupling device 11 provided at the most distal end of body 10. Coupling device 11 may be a luer-lock type cap or a twist-on locking device, and is configured to receive a syringe needle or the luer-lock coupling of a three-way stop cock.

Inner syringe body 20 has a diameter smaller than that of the outer syringe body 10. A shaft or plunger rod 22 provided within the body 20 permits the syringe body 20 to be filled with the fluid sample 60 when it flows from the outer syringe body 10 to the inner syringe 20 by passing through the flow-through plunger 12.

Preferably, the autologous plasma 60 in the inner syringe body 20 contains an amount of thrombocytes that provides enhancement of the healing of the damaged tissue and promote tissue growth. Once plasma 60 is injected into the tissue with the syringe 20, the thrombocytes excrete growth factors that will trigger/enhance the healing process. The high level of thrombocytes also enhances the healing of the damaged tissue and tissue growth.

Preferably, the autologous conditioned plasma 60 in the inner syringe body 20 has a platelet concentration factor of about 2 compared to that of the patient's normal blood. In an exemplary embodiment, the autologous conditioned plasma (ACP) may contain about 470,000 platelet/microliter (for a donor) compared to the about 200,000-400,000 platelet/microliter of the donor's whole blood; and compared to the about 500,000-1,000,000 platelet/microliter of the platelet-rich plasma (PRP) (of the donor); and compared to about 0 platelet/microliter of the platelet-poor plasma (PPP) (of the donor). Autologous conditioned plasma (ACP) 60 (shown in FIGS. 1(c)-1(f)) may be obtained by subjecting a volume of about 10 ml blood (of a donor) for about 1 spin in the apparatus 100, to obtain a harvest volume of about 2-4 ml autologous conditioned plasma (ACP), which in turn contains about 470,000 platelet (thrombocyte)/microliter.

The autologous conditioned plasma 60 may be employed for treatment of various cartilage or tendon damage or diseases (as long as the cartilage is partially remaining) such as, for example:
  1. Chondromalacia I°-III° (according to Outerbridge);
     a. Large and small joints of upper and lower extremities; and
     b. Small vertebral joints.
  2. Traumatologic cartilage damage;
  3. Post-op situations e.g. flake fracture-refixation, microfractures and/or cartilage transplantation (ACT or OATS); and
  4. Tendinosis and ligamentosis.

The autologous conditioned plasma 60 may be also employed in neurosurgery applications, such as, for example:
  1. Radiculitis and radiculopathy of the cervical and lumbar spine;
  2. Syndrome of the vertebral column facets; and
  3. Other spinal applications, e.g., degeneration of spinal disk and erosive osteochondrosis.

The method of the present invention comprises the steps of: (i) providing an extraction assembly comprising an outer syringe body 10 and an inner syringe body 20, at least a portion of the inner syringe body being disposed within a portion of the outer syringe body; (ii) drawing autologous blood 50 from the animal/patient by employing the outer syringe body 10; (iii) conducting a centrifugation step of the autologous blood 50 from the outer syringe body 10 to obtain an autologous conditioned plasma 60 from the autologous blood 50; (iv) removing, with the inner syringe body 20, at least a portion of the autologous conditioned plasma 60 from the outer syringe body 10; and (v) delivering at least a portion of the autologous conditioned plasma 60 into a damaged tissue of the animal, by employing the inner syringe body 20.

The autologous conditioned plasma 60 extracted with the inner syringe body 20 may be administered to a patient by injection once a week, for a total of about six weeks. In individual cases, however, the autologous conditioned plasma 60 may be administered twice a week. In neurological applications, the autologous conditioned plasma 60 of the present invention may be provided by assisted injections upon the relevant nerve roots. Alternatively, the autologous conditioned plasma 60 may be provided on or between the vertebral joints.

The autologous conditioned plasma 60 of the present invention may be prepared/obtained directly in a doctor's office as well as in the operating room. In addition, by employing only a double-chamber syringe (or a first syringe in direct fluid communication with a second syringe) and not a plurality of syringes, the need for additional syringes and storage containers is eliminated, and the contamination risk is reduced. A main advantage of the method of obtaining the autologous conditioned plasma 60 of the present invention is that the double syringe 100, 200 enables to transfer plasma from the bigger syringe into the smaller syringe without handling several syringes. Further, as no activator (such as thrombin, for example) is added to the extracted blood to initiate or catalyze a platelet release reaction (i.e., no activator or substance to release material from the platelets is added prior to, or during, the centrifugation process), the risk of contamination is additionally reduced and the complexity of the procedure is decreased.

According to an exemplary embodiment, activators (such as thrombin, for example) may be added subsequent to the harvesting of the autologous conditioned plasma (ACP) (i.e., subsequent to the centrifugation process) to force the platelets to secrete their growth factors.

Although the present invention has been described in connection with preferred embodiments, many modifications and variations will become apparent to those skilled in the art. While preferred embodiments of the invention have been described and illustrated above, it should be understood that these are exemplary of the invention are not to be considered as limiting. Accordingly, it is not intended that the present invention be limited to the illustrated embodiments, but only by the appended claims.

What is claimed as new and desired to be protected by Letters Patent of the United States is:

1. A method of obtaining autologous, platelet enriched plasma, comprising:
    providing a two-chamber syringe assembly comprising a first syringe having a first body with a first diameter; and a second syringe having a second body with a second diameter smaller than the first diameter, the first syringe being in direct fluid communication with the second syringe, and the second syringe being located within the first syringe;
    withdrawing blood with the first syringe;
    subjecting the syringe assembly to centrifugation to obtain an autologous, platelet enriched plasma; and
    transferring at least a portion of the autologous, platelet enriched plasma from the first syringe to the second syringe.

2. The method of claim 1, wherein the blood contains a first amount of platelets/microliter and wherein the autologous, platelet enriched plasma contains a second amount of platelets/microliter, wherein the second amount is about twice the first amount.

3. The method of claim 1, wherein the blood contains about 200,000 platelets/microliter and wherein the autologous, platelet enriched plasma contains about 400,000-470,000 platelets/microliter.

4. The method of claim 1, further comprising treating at least a portion of a damaged tissue with the autologous, platelet enriched plasma to facilitate healing of the tissue.

5. The method of claim 4, wherein the treating of the damaged tissue further comprises removing the second syringe from the syringe assembly and injecting, with the second syringe, the autologous, platelet enriched plasma into the damaged tissue.

6. The method of claim 4, wherein the damaged tissue is a joint.

7. The method of claim 4, wherein the damaged tissue is a nerve root or a vertebral joint.

8. The method of claim 4, wherein the damaged tissue is a damaged tendon.

9. A method of surgical treatment of connective tissue injury, comprising:
    providing a double-chamber syringe comprising a first chamber having a first body with a first diameter; and a second chamber connected to the first chamber and in fluid communication with the first chamber, the second chamber having a second body with a second diameter smaller than the first diameter, the second chamber being located at least partially within the first chamber;
    withdrawing autologous blood with the double-chamber syringe so that the autologous blood is temporarily stored within the first chamber;
    introducing the double-chamber syringe into a centrifuge and centrifuging the double-chamber syringe to obtain an autologous, platelet enriched plasma in the first chamber;
    transferring at least a portion of the autologous, platelet enriched plasma from the first chamber to the second chamber;
    disconnecting the second chamber with the autologous, platelet enriched plasma from the first chamber; and
    delivering the autologous, platelet enriched plasma to the connective tissue.

10. The method of claim 9, wherein the autologous blood contains a first amount of platelets/microliter and wherein the autologous, platelet enriched plasma contains a second amount of platelets/microliter, the second amount being about twice the first amount.

11. The method of claim 9, wherein the autologous blood contains about 200,000 platelets/microliter and wherein the autologous, platelet enriched plasma contains about 400,000-470,000 platelets/microliter.

12. The method of claim 9, wherein the connective tissue is selected from the group consisting of nerve root, vertebral joint, cartilage and tendon.

13. The method of claim 9, wherein the autologous, platelet enriched plasma is employed for treating chondromalacia I°-III°, cartilage damage, cartilage transplantation, tendinosis, ligamentosis, radiculitis, radiculopathy of the cervical or lumbar spine, syndrome of the vertebral column facets, degeneration of spinal disk, or erosive osteochondrosis.

* * * * *